(12) United States Patent
Grimm et al.

(10) Patent No.: US 11,452,601 B2
(45) Date of Patent: Sep. 27, 2022

(54) WIRE ANNULOPLASTY RING

(71) Applicant: Medtronic Vascular, Inc., Santa Rosa, CA (US)

(72) Inventors: Emily Grimm, Petaluma, CA (US); Caitlin Dorff, Santa Rosa, CA (US); Karan Punga, San Rafael, CA (US); Matthew E. Genovese, Windsor, CA (US); Olivia Metcalf, Santa Rosa, CA (US); Fatemeh Fatemi Far, Santa Rosa, CA (US); William Berthiaume, Santa Rosa, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 0 days.

(21) Appl. No.: 16/710,835

(22) Filed: Dec. 11, 2019

(65) Prior Publication Data
US 2020/0188108 A1   Jun. 18, 2020

Related U.S. Application Data

(60) Provisional application No. 62/779,258, filed on Dec. 13, 2018.

(51) Int. Cl.
*A61F 2/24* (2006.01)

(52) U.S. Cl.
CPC .......... *A61F 2/2445* (2013.01); *A61F 2/2466* (2013.01); *A61F 2210/0014* (2013.01); *A61F 2210/0023* (2013.01); *A61F 2220/0016* (2013.01); *A61F 2230/0013* (2013.01); *A61F 2230/0017* (2013.01)

(58) Field of Classification Search
CPC .... A61F 2/2445; A61F 2/2442; A61F 2/2448; A61F 2/2466
See application file for complete search history.

(56) References Cited

U.S. PATENT DOCUMENTS

| | | | |
|---|---|---|---|
| 8,430,926 B2 | 4/2013 | Kirson | |
| 8,795,352 B2 | 8/2014 | O'Beirne et al. | |
| 9,517,130 B1 | 12/2016 | Alon et al. | |
| 2002/0087173 A1 | 7/2002 | Alferness et al. | |
| 2004/0236419 A1* | 11/2004 | Milo | A61B 17/0401 |
| | | | 623/2.36 |
| 2005/0125011 A1 | 6/2005 | Spence et al. | |

(Continued)

OTHER PUBLICATIONS

International Search Report and Written Opinion of International Application No. PCT/US2019/065891, dated Feb. 5, 2020, 8 pp.

(Continued)

*Primary Examiner* — Brian A Dukert
*Assistant Examiner* — Rebecca Lynee Zimmerman
(74) *Attorney, Agent, or Firm* — Medler Ferro Woodhouse & Mills PLLC

(57) ABSTRACT

The disclosure describes an annuloplasty device that includes a wire configured to extend around at least part of an annulus of a cardiac or vascular valve, such as at least partially around a circumference of the annulus, and a plurality of anchors. The anchors of the plurality of anchors are configured to engage the wire and anchor the wire to the annulus. The wire is configured to urge at least some anchors of the plurality of anchors toward each other in a radially inward direction to decrease a distance between valve leaflets that extend from the annulus.

9 Claims, 8 Drawing Sheets

(56) References Cited

U.S. PATENT DOCUMENTS

| | | |
|---|---|---|
| 2005/0137700 A1 | 6/2005 | Spence et al. |
| 2009/0259307 A1 | 10/2009 | Gross et al. |
| 2010/0030328 A1* | 2/2010 | Seguin .................. A61F 2/2445 623/2.11 |
| 2010/0292785 A1* | 11/2010 | Seguin ............. A61B 17/00234 623/2.11 |
| 2011/0166649 A1 | 7/2011 | Gross et al. |
| 2012/0053680 A1 | 3/2012 | Bolling et al. |
| 2012/0296417 A1* | 11/2012 | Hill ....................... A61F 2/2445 623/2.11 |
| 2012/0296419 A1 | 11/2012 | Richardson et al. |
| 2015/0127096 A1 | 5/2015 | Rowe et al. |
| 2015/0366556 A1 | 12/2015 | Khairkhahan et al. |
| 2018/0008409 A1 | 1/2018 | Kutzik et al. |
| 2018/0161161 A1 | 6/2018 | Yellin et al. |

OTHER PUBLICATIONS

U.S. Appl. No. 16/710,987, filed Dec. 11, 2019, naming inventors Metcalf et al.
Extended European Search Report, European Application No. 19894554.5, dated Jul. 25, 2022.

* cited by examiner

FIG. 6A
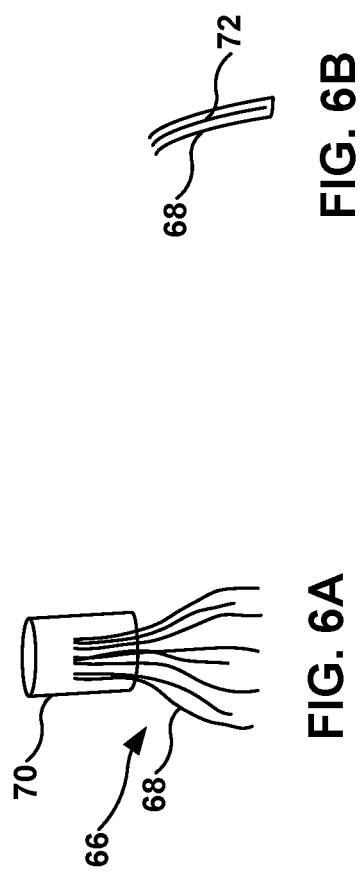
FIG. 6B
FIG. 6C
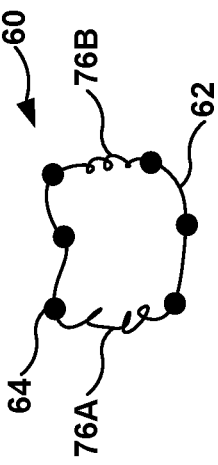
FIG. 6D
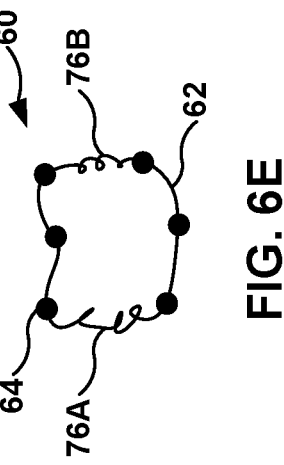
FIG. 6E
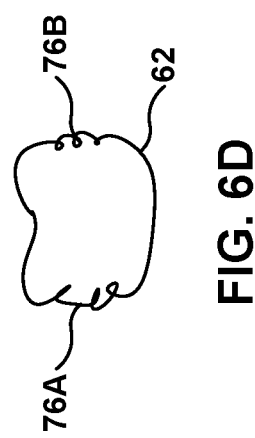

WIRE ANNULOPLASTY RING

This application claims the benefit of U.S. Provisional Patent Application Ser. No. 62/779,258, filed on Dec. 13, 2018, the entire content of which is incorporated by reference herein.

TECHNICAL FIELD

This disclosure relates to heart valve repair, such as mitral valve repair.

BACKGROUND

Some patient conditions can produce valvular insufficiency or regurgitation. Valvular insufficiency or regurgitation occurs when a valve in a heart of a subject does not close completely, allowing blood to flow backwards (e.g., from the left ventricle to the left atrium), which may adversely impact the functionality of the heart.

The mitral valve includes two leaflets (anterior and posterior) attached to an annulus (e.g., a fibrous ring). In a healthy heart, the mitral valve leaflets close, or coapt, during contraction of the left ventricle and prevent blood from flowing back into the left atrium. Mitral valve regurgitation is a condition in which the leaflets of a mitral valve of a subject do not coapt properly and, as a result, blood regurgitates back into the left atrium from the left ventricle. The regurgitation of blood back into the left atrium may result in a reduced ejection volume from the left ventricle, causing the heart of the subject to work relatively hard to supply the desirable volume of blood to the body. Mitral regurgitation may occur because of different patient conditions. For example, secondary mitral regurgitation, also referred to as functional mitral regurgitation, may occur when a left ventricle dilates and causes dilation of the mitral annulus of a subject.

SUMMARY

In some aspects, this disclosure describes example annuloplasty devices, systems, and techniques for repairing a heart valve, such as, but not limited to, a mitral valve. The annuloplasty devices, systems, and techniques enable reduction in spacing between valve leaflets, may improve coaptation of the valve leaflets, and may help reduce valvular insufficiency or regurgitation.

The details of one or more examples are set forth in the accompanying drawings and the description below. Other features, objects, and advantages of examples according to this disclosure will be apparent from the description and drawings, and from the claims.

BRIEF DESCRIPTION OF THE DRAWINGS

FIGS. 6A-6E are schematic views of an example annuloplasty device including a wire and a plurality of anchors, and a wire frame including a plurality of hollow tubular struts.

DETAILED DESCRIPTION

This disclosure describes devices, systems, and techniques for repairing a heart valve, such as, but not limited to, a mitral valve. The annuloplasty devices, systems, and techniques enable reduction in spacing between valve leaflets, may improve coaptation of the valve leaflets, and may reduce valvular insufficiency or regurgitation. Annuloplasty devices may include a wire and a plurality of anchors. The plurality of anchors may be configured to engage the wire and tissue of an annulus of the heart valve or trigone of the heart valve to fix the wire to the tissue. The wire may be configured to exert a radially inward force on the plurality of anchors to exert a force on the tissue and urge the valve leaflets toward each other and improve coaptation of the valve leaflets.

The wire may exert the radially inward force on the plurality of anchors in one or more of a variety of manners. For example, the wire may be attached to a first anchor of the plurality of anchors and engaged with other anchors of the plurality of anchors. The wire then may be manipulated by a delivery device to reduce a length of the wire and attach the wire to a second anchor of the plurality of anchors. This may draw the plurality of anchors towards each other, exerting the radially inward force on the plurality of anchors and the tissue.

As another example, the wire may include at least one integral feature that causes a shortening of the wire once the wire is released from a delivery device and engaged with the plurality of anchors. For example, the wire may include at least one spring or coil that causes an effective shortening of the distance between at least some anchors of the plurality of anchors to cause the anchors to exert the radially inward force on the tissue. As an additional example, the wire may have a pre-set shape with a radius of curvature smaller than a radius of curvature of the annulus (e.g., a curve tracing the positions of the plurality of anchors), which may urge the plurality of anchors radially inward to exert the radially inward force on the tissue. In this way, the annuloplasty device may enable reduction in spacing between valve leaflets, improve coaptation of the valve leaflets, and reduce valvular insufficiency or regurgitation.

Figure 1A:
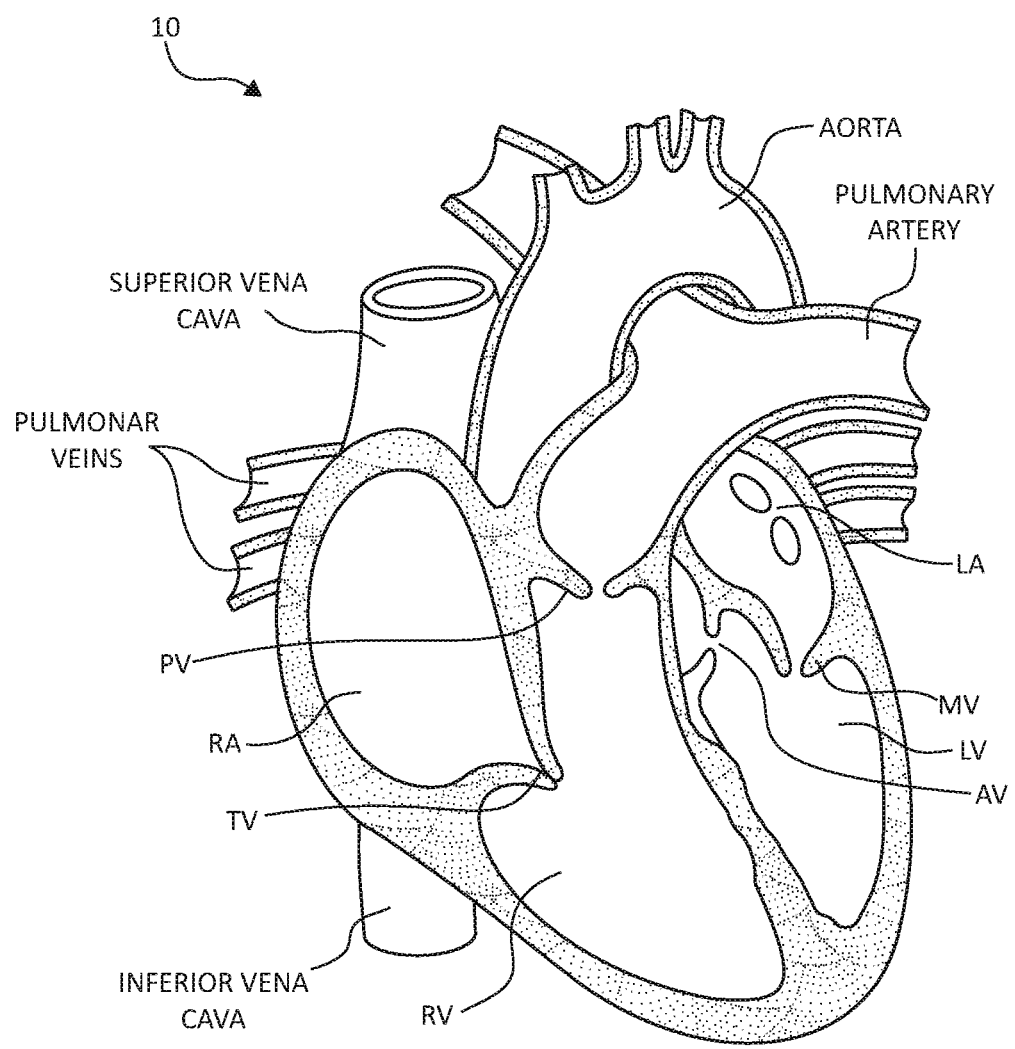
FIGS. 1A and 1B are schematic cross-sectional views of an example human heart.
Figure 1B:
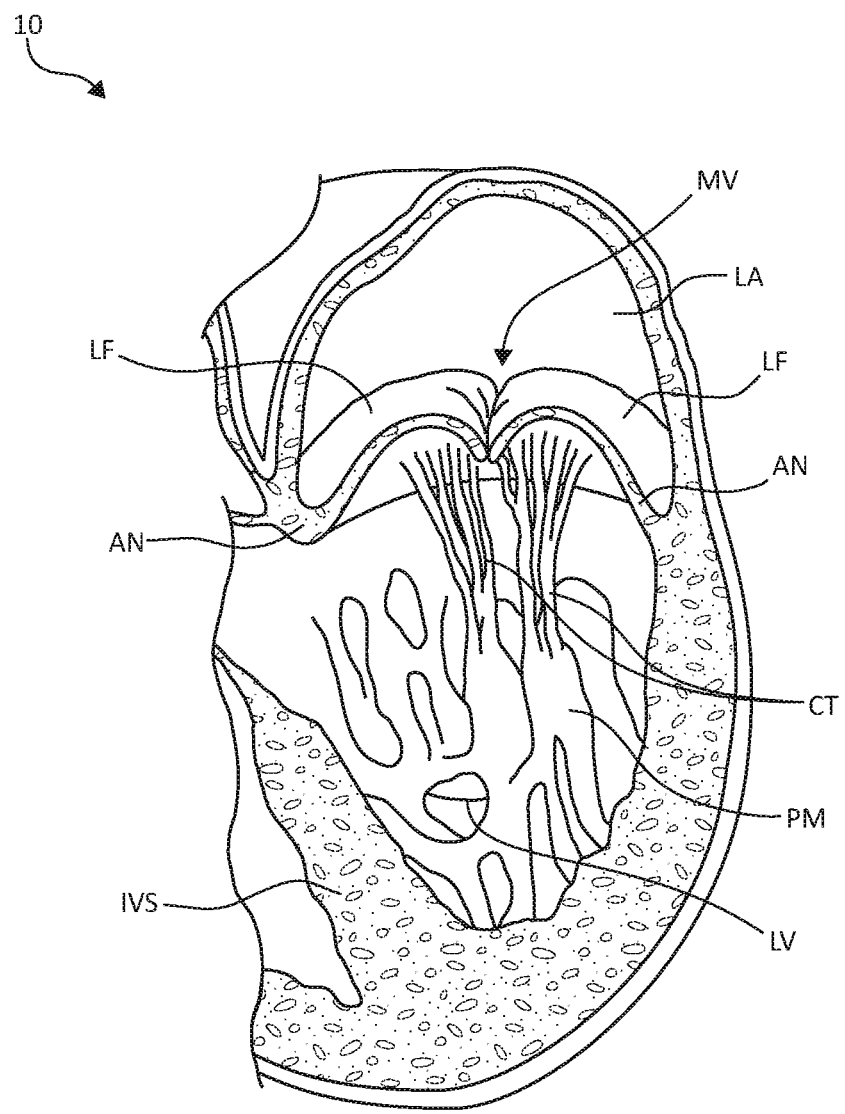

FIGS. 1A and 1B are schematic cross-sectional views of an example human heart 10. The human heart 10 is a four chambered, muscular organ that provides blood circulation through the body during a cardiac cycle. The four main chambers include the right atrium (RA) and right ventricle (RV) which supplies the pulmonary circulation, and the left atrium (LA) and left ventricle (LV) which supplies oxygenated blood received from the lungs to the remaining body. To ensure that blood flows in one direction through the heart, atrioventricular valves (tricuspid valve (TV) and mitral valves (MV)) are present between the junctions of the atrium and the ventricles, and semi-lunar valves (pulmonary valve (PV) and aortic valve (AV)) govern the exits of the ventricles leading to the lungs and the rest of the body. These valves contain leaflets (LF) or cusps that open and shut in response to blood pressure changes caused by the contraction and relaxation of the heart chambers. FIG. 1B is a schematic sectional illustration of a left ventricle LV of heart 10 showing anatomical structures and a native mitral valve MV.

The left atrium LA receives oxygenated blood from the lungs via the pulmonary veins and pumps the oxygenated blood through the mitral valve MV and into the left ventricle LV during ventricular diastole. The left ventricle LV contracts during systole and blood flows outwardly through the aortic valve AV, into the aorta and to the remainder of the body. In a healthy heart, the leaflets LF of the native mitral valve MV meet evenly at the free edges or "coapt" to close and prevent back flow of blood into the left atrium LA during contraction of the left ventricle LV. The tissue of the leaflets LF attach to the surrounding heart structure via a dense fibrous ring of connective tissue called an annulus AN. The flexible tissue of the leaflets LF of the native mitral valve MV are connected to papillary muscles PM, which extend upwardly from the lower wall of the left ventricle LV and the interventricular septum IVS, via branching tendons called chordae tendinae CT.

Mitral valve regurgitation is a condition in which the leaflets of a mitral valve of a subject do not coapt properly and, as a result, blood regurgitates back into the left atrium LA from the left ventricle LV. The regurgitation of blood back into the left atrium LA may result in a reduced ejection volume from the left ventricle LV, causing the heart of the subject to work relatively hard to supply the desirable volume of blood to the body. Mitral regurgitation may occur because of one or more patient conditions. For example, secondary mitral regurgitation, also referred to as functional mitral regurgitation, may occur when the left ventricle LV dilates and causes dilation of the mitral annulus of a subject. The leaflets LF of the valves may move apart as a result of the dilation of the left ventricle LV, which may adversely impact the ability of the leaflets LF to properly coapt.

In addition to or instead of being caused by dilation of the left ventricle LV, mitral valve regurgitation (or other valve regurgitation) may be caused by calcified plaque buildup in heart 10. For example, the leaflets LF of the valves (e.g., aortic valve AV or mitral valve MV) may harden and may not sufficiently coapt or meet, such that regurgitation may occur where the valve does not close completely, allowing blood to flow backwards (e.g., from the left ventricle LV to the left atrium LA). The left side of heart 10 (e.g., mitral valve MV and aortic valve AV) can be more likely to become calcified because of the higher pressures generated.

The medical devices, systems, and techniques described herein may be used to repair a valve of heart 10 via a minimally invasive medical procedure, e.g., via a transcatheter, trans-septal medical procedure that is less invasive than open heart surgery. While open heart surgeries, such as annuloplasty performed via open heart surgery, may have positive outcomes, a more minimally invasive medical procedure may also have positive outcomes while also being associated with a shorter recovery time for some patients compared to open heart surgery.

Although example devices, systems, and techniques are primarily described herein with reference to the mitral valve MV, in other examples, the example devices, systems, and techniques may be used to repair other valves in heart 10.

Figure 2:
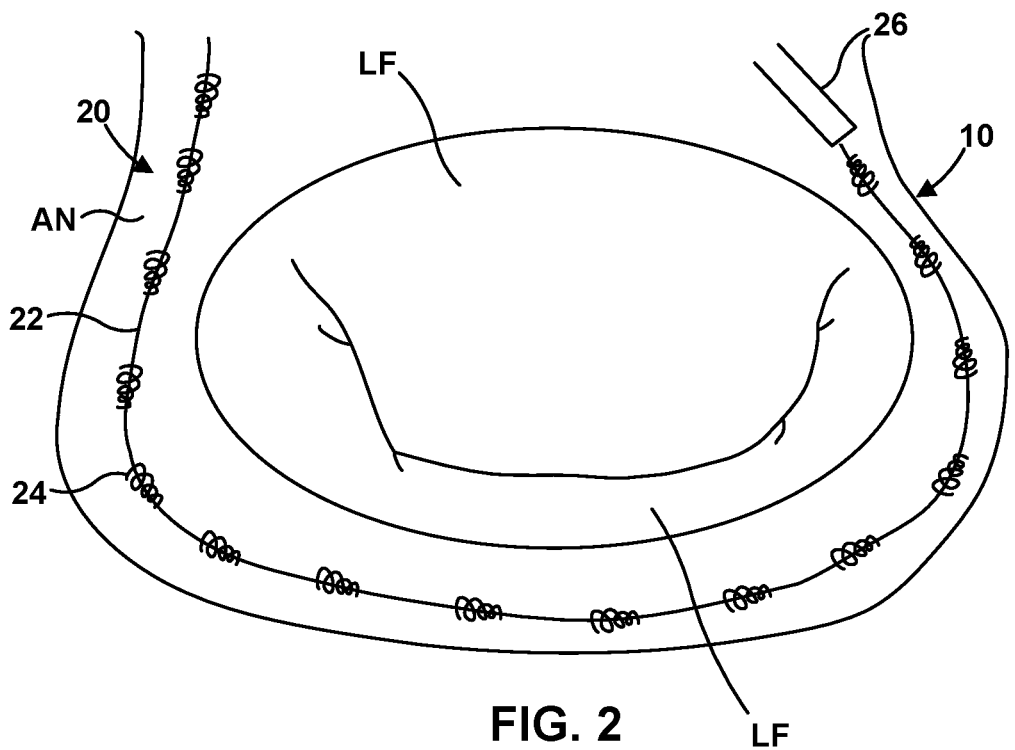
FIG. 2 is a schematic cross-sectional view of an example human heart and an example annuloplasty device including a wire and a plurality of anchors.

FIG. 2 is a schematic cross-sectional view of an example human heart 10 (e.g., showing the annulus AN of mitral valve MV (FIGS. 1A and 1B) and leaflets LF) and an annuloplasty device 20 including a wire 22 and a plurality of anchors 24. Leaflets LF may include an anterior leaflet and a posterior leaflet.

Wire 22 may include a biocompatible material that is configured to apply or maintain a force on annulus AN and/or leaflets LF to urge leaflets LF toward each other and improve coaptation of leaflets LF. In some examples, wire 22 may include a biocompatible metal or alloy, such as nitinol, stainless steel, a cobalt-chromium alloy, or the like. In other examples, wire 22 may include a polymer, a suture, a composite, a metal, or any combination of suitable materials. For example, wire 22 may consist essentially of a metal. As another example, wire 22 may be formed from poly-paraphenylene terephthalamide (e.g., Kevlar, DuPont, Wilmington, Del.). In some instances, wire 22 may include a biocompatible shape memory alloy. In addition to or instead of a metal, in some examples, wire 22 may comprise a polymer. For example, wire 22 may consist essentially of a polymer or may be formed from a composite of metal or polymer.

In some examples, wire 22 may have a pre-set shape. For example, the pre-set shape may be defined using a heat treatment. The pre-set shape is a shape toward which wire 22 recovers in the absence of an applied force. In some examples, the pre-set shape may include a radius of curvature larger than a curvature of annulus AN, such that the pre-set shape urges wire 22 radially outward toward walls of annulus AN to enable wire 22 to more closely follow the shape of annulus AN and conform to the annulus AN. In other examples, the pre-set shape may include a radius of curvature smaller than a curvature of annulus AN, such that the pre-set shape urges wire 22 radially inward toward coaptation surfaces of leaflets LF. When wire 22 is anchored to annulus AN and/or leaflets LF, the pre-set shape that urges wire 22 radially inward toward may exert a force on annulus AN and/or leaflets LF to urge annulus AN to reduce in circumference and increase coaptation of leaflets LF.

Wire 22 is configured to extend along a predetermined length (e.g., at least part of a circumference) of annulus AN. In some examples, wire 22 may extend from a first trigone attached to annulus AN to a second trigone attached to annulus AN. In other examples, wire 22 may extend from adjacent to a first leaflet LF to a second leaflet LF. In still other examples, wire 22 may extend substantially around a perimeter of annulus AN.

In some examples, annuloplasty device 20 includes a plurality of wires 22. For example, at least two of the wires may overlap with each other (e.g., each of the wires may extend the same length of annulus AN such that the wires fully overlap or each of the wires may only partially overlap and extend along different lengths of annulus AN). As another example, the wires may not overlap at all and may instead be positioned to be extend along different portions of annulus and define a discontinuous annuloplasty device. For example, a first wire may be configured to extend from adjacent a first trigone to adjacent a second trigone of the cardiac or vascular valve in a first direction, and a wire may be configured to extend from adjacent the first trigone to adjacent the second trigone of the cardiac or vascular valve in a second direction opposite the first direction. In any multi-wire example, the wires may be physically separate from each other or may be connected to each other with a fabric or other relatively compliant material.

Annuloplasty device 20 also includes a plurality of anchors 24. The plurality of anchors 24 may include any structures configured to engage wire 22 to annulus AN and/or leaflets LF and retain wire 22 substantially in place relative to annulus AN and/or leaflets LF. Respective anchors of the plurality of anchors may be positioned along a length of wire 22. In some examples, plurality of anchors 24 may be fluorogenic, echogenic, or both.

In some examples, the plurality of anchors 24 include a plurality of helices or double helices that are configured to be advanced into tissue of heart 10, e.g., annulus AN and/or leaflets LF. In other examples, the plurality of anchors 24 may include push anchors. The plurality of anchors 24 may optionally include an attachment feature, such as a hook, loop, or the like that is configured to engage wire 22 or another portion of annuloplasty device 20 to substantially retain wire 22 relative to the anchor 24. In this way, the plurality of anchors 24 may be configured to substantially retain wire 22 relative to respective locations of tissue of heart 10, such as a location of annulus AN and/or leaflets LF. The plurality of anchors 24 thus allow application of force from wire 22 to tissue of heart 10 at selected locations of heart 10.

While helical anchors 24 are primarily described herein, in other examples, the anchors may have another suitable configuration that enables the anchor to engage with tissue and substantially fix to the tissue, such as, but not limited to, a barb, a hook, a tine, and the like.

The plurality of anchors 24 may include a biocompatible material that is configured to engage wire 22 and transfer force from wire 22 to annulus AN and/or leaflets LF to urge leaflets LF toward each other and improve coaptation of leaflets LF. In some examples, the plurality of anchors 24 may include a biocompatible metal or alloy, such as nitinol, stainless steel, a cobalt-chromium alloy, or the like. In some instances, the plurality of anchors 24 may include a biocompatible shape memory alloy. In addition to or instead of a metal, in some examples, anchors 24 may be formed at least partially from a polymer.

In the example of FIG. 2, the plurality of anchors 24 include a plurality of helices. In some examples, the helices may be conical helices that decrease in diameter from a first, wide end of the conical helix to a second, narrow end of the conical helix. Each respective helix defines a respective longitudinal axis parallel to a length of the respective helix. Each respective helix is configured to be engaged with wire 22 such that wire 22 extends through a bore (e.g., internal lumen) of the respective helix substantially parallel to the longitudinal axis of the helical coil.

In some examples, a wide end of a conical helix may be positioned toward a distal end of wire 22 (e.g., an end of wire 22 that exits delivery device 26 first). This may facilitate engagement of the plurality of anchors 24 with tissue of annulus AN, e.g., by torquing the plurality of anchors 24 around wire 22 to screw the plurality of anchors 24 into the tissue.

FIG. 2 also illustrates a delivery device 26 for annuloplasty device 20. In the example of FIG. 2, delivery device 26 includes a catheter. The catheter may define an internal lumen that extends from proximate a proximal end of the catheter to proximate a distal end of the catheter (e.g., may extend from the proximal end to the distal end). The lumen may be configured to house annuloplasty device 20 during percutaneous introduction of the catheter into vasculature of a patient and advancing of the distal end of the catheter to the treatment location, such as the left atrium LA. In some examples, the catheter may be used with a guidewire, a guide catheter, or the like, to facilitate introducing the catheter into vasculature of a patient and advancing the distal end of the catheter to the treatment location. In some examples, the catheter includes a steerable shaft and/or distal tip to allow a clinician to control positioning of the distal tip relative to anatomical structures, such as heart 10. In some implementations, the catheter may access left atrium LA trans-septally.

The catheter is also configured to deploy annuloplasty device 20, e.g., wire 22 and plurality of anchors 24 in position proximate annulus AN and engage the plurality of anchors 24 with tissue of heart 10, e.g., with annulus AN and/or leaflets LF. In some examples, to facilitate positioning of the catheter, annuloplasty device 20, or both, within the treatment location, a distal portion of the catheter may include at least one radiographic marker configured to be visualized using a radiographic technique.

In some examples, the plurality of anchors 24 may be pre-engaged or pre-assembled with wire 22 such that wire 22 and the plurality of anchors 24 are assembled within the lumen of (a single) delivery device 26. A clinician may manipulate delivery device 26 to release a first portion of wire 22 and a first anchor of the plurality of anchors 24 and may manipulate delivery device 26 to manipulate the first anchor, wire 22, or both, to engage the first anchor of the plurality of anchors 24 with tissue. The clinician then may manipulate delivery device 26 to release a second portion of wire 22 and a second anchor of the plurality of anchors 24 and may manipulate delivery device 26 to engage the second anchor of the plurality of anchors 24 with tissue. The clinician may continue this process until an entire length of wire 22 and all anchors 24 have been released from delivery device 26.

In other examples, at least some of the plurality of anchors 24 may be delivered separately from wire 22. For example, delivery device 26 may be a first delivery device that is configured to house and release wire 22 into approximate position adjacent annulus AN. A clinician may track the first delivery device along the shape of annulus AN to position wire 22. In some examples, a distal end of wire 22 may define or be attached to a first anchor, and the clinician may use the first delivery device to engage the first anchor to tissue at a selected location to temporarily and/or partially anchor wire 22 to tissue until other or more anchors 24 are engaged to wire 22 and tissue.

The clinician then may remove the first delivery device and advance a second delivery device that is configured to house and release the plurality of anchors 24. For example, wire 22 may act as a guide for the second delivery device and the clinician may advance the second delivery device over wire 22 from a proximal end of wire 22 toward a distal end of wire 22. The clinician may manipulate the second delivery device to release an anchor and torque the anchor to engage the anchor with tissue. The clinician then may move the second delivery device to a second location over wire 22, manipulate the second delivery device to release an anchor, and manipulate the second delivery device to torque the anchor to engage the anchor with tissue. The clinician may repeat this procedure until all anchors of the plurality of anchors 24 are engaged with wire 22 and tissue.

In some examples of annuloplasty device 20 including at least two wires 22, one wire 22 may act as a guide for the second delivery device and the other wire 22 may be used to cinch the anchors towards each other.

Regardless of whether the plurality of anchors 24 are pre-assembled with wire 22 or delivered using a second delivery device, once the plurality of anchors 24 are engaged with wire 22 and tissue, the clinician may manipulate a delivery device (e.g., the single delivery device 26 used to release both wire 22 and plurality of anchors 24, the first delivery device used to release wire 22, or the second delivery device used to release the plurality of anchors 24) to pull wire 22 and cinch the plurality of anchors 24 radially inward toward each other. This may exert a force on annulus AN and leaflets LF that causes leaflets LF to coapt more completely. The clinician then may manipulate a delivery device to attach the wire (e.g., cut and tie the wire) to one or more respective anchors of the plurality of anchors 24 to fix wire 22 in place and maintain the cinching force.

Figure 3:
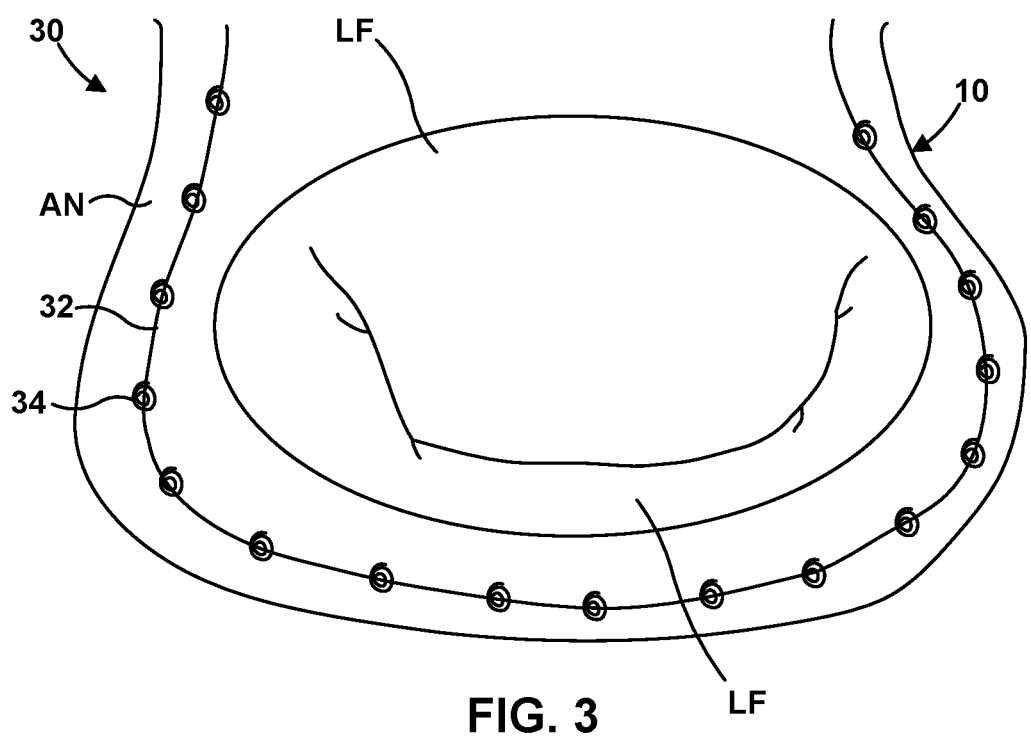
FIG. 3 is a schematic cross-sectional view of an example human heart and an example annuloplasty device including a wire and a plurality of anchors.

In some examples, rather than the plurality of anchors being oriented with a longitudinal axis substantially parallel to a length of wire 22, the plurality of anchors may be oriented with a longitudinal axis canted to a length of wire 22. FIG. 3 is a schematic cross-sectional view of an example human heart 10 and an annuloplasty device 30 including a wire and a plurality of anchors. Wire 32 may be similar to or substantially the same as any other wires described herein, including wire 22 of FIG. 2, aside from differences described herein. Similarly, plurality of anchors 34 may be similar to or substantially the same as any other anchors described herein, including plurality of anchors 24 of FIG. 2, aside from differences described herein.

The plurality of anchors 34 may include helices, double helices, hooks, or the like, and may include or omit an optional attachment feature for engaging wire 32. In addition, each anchor of the plurality of anchors may be engaged with tissue by, for example, "screwing" the anchor into tissue using a torquing force, by pushing the anchor into tissue using a pushing force, by suturing the anchor to tissue, or any combination thereof. In some examples, plurality of anchors 34 may include conical helices, conical double helices, or the like. Instead of being oriented with a longitudinal axis substantially parallel to a length of wire 22, the plurality of anchors 34 may be oriented with longitudinal axes canted to a length of wire 22. In some examples, the longitudinal axes of the plurality of anchors 34 may be oriented substantially perpendicular to a length of wire 22. In other examples, the longitudinal axes of the plurality of anchors 34 may be oriented at an angle less than or greater than 90 degrees relative to a length of wire 22. In examples in which the plurality of anchors 34 include conical helices or conical double helices, a wide end of the respective conical helix or conical double helix may be oriented to engage tissue of annulus AN or may be oriented away from tissue of annulus AN such that a narrow end of the respective conical helix or conical double helix engages tissue of annulus AN.

Wire 32 and the plurality of anchors 34 may be delivered using one or more delivery device, similar to wire 22 and the plurality of anchors 24 of FIG. 2. For example, the plurality of anchors 34 may be pre-engaged or pre-assembled with wire 32 such that wire 32 and the plurality of anchors 34 can be assembled within the inner lumen of a single delivery device. A clinician may manipulate the single delivery device to release a first portion of wire 32 and a first anchor of the plurality of anchors 34 and may manipulate the delivery device to engage the first anchor of the plurality of anchors 34 with tissue, e.g., by torquing the first anchor to screw it into tissue. The clinician then may manipulate the single delivery device to release a second portion of wire 32 and a second anchor of the plurality of anchors 34 and may manipulate the single delivery device to engage the second anchor of the plurality of anchors 34 with tissue. The clinician may continue this process until an entire length of wire 32 and all anchors 34 have been released from the delivery device.

In other examples, at least some of the plurality of anchors 34 may be delivered separately from wire 32. For example, a first delivery device may be configured to house and release wire 32 into approximate position adjacent annulus AN. For example, a clinician may track the first delivery device along the shape of annulus AN to position wire 32. In some examples, a distal end of wire 32 may be attached to a first anchor, and the clinician may use the first delivery device to engage the first anchor to tissue at a selected location to temporarily and/or partially anchor wire 32 to tissue until other or more anchors 34 are engaged to wire 32 and tissue.

The clinician then may remove the first delivery device and advance a second delivery device that is configured to house and release the plurality of anchors 34. For example, the clinician may advance the second delivery device over wire 32 from a proximal end of wire 32 toward a distal end of wire 32. The clinician may manipulate the second delivery device to release an anchor and torque the anchor to engage the anchor with tissue. The clinician then may move the second delivery device to a second location over wire 32, manipulate the second delivery device to release an anchor, and manipulate the second delivery device to torque the anchor to engage the anchor with tissue. The clinician may repeat this procedure until all anchors of the plurality of anchors 34 are engaged with wire 32 and tissue.

In other examples, annuloplasty device 30 may be delivered using a single delivery device that includes at least two lumens. First and second lumens of the delivery device may be, for example, substantially parallel to each other. The first lumen may be configured to house wire 32, and the second lumen may be configured to house the plurality of anchors 34. In some examples, the second lumen may be configured to house the plurality of anchors 34 with respective long axes of the plurality of anchors substantially parallel to a longitudinal axis of the second lumen.

The first and second lumen may be coupled (e.g., mechanically attached) such that wire 32 passes through the second lumen before exiting the delivery device. For example, wire 32 may pass through the second lumen substantially perpendicular to the longitudinal axis of the second lumen. As the plurality of anchors 34 may be housed with respective long axes of the plurality of anchors substantially parallel to a longitudinal axis of the second lumen, wire 32 may pass through a bore of a respective anchor of the plurality of anchors 34 to engage wire 32 with the respective anchor. The delivery device may be positioned with the exit of the second lumen substantially perpendicular to annulus AN and the respective anchor may be delivered and engaged with tissue of annulus AN by the delivery device. A delivery device including two lumens may enable wire 32 to be cinched or tightened as wire 32 is delivered to annulus AN (e.g., after delivery and engagement of a respective anchor with annulus AN).

Regardless of whether the plurality of anchors 34 are pre-assembled with wire 32 or delivered using a second delivery device or a second lumen of a delivery device, once the plurality of anchors 34 are engaged with wire 32 and tissue, the clinician may manipulate a delivery device (e.g., the single delivery device used to release both wire 32 and plurality of anchors 24, the first delivery device used to release wire 32, or the second delivery device used to release the plurality of anchors 34) to pull wire 32 and cinch the plurality of anchors 34 radially inward toward each other. This may exert a force on annulus AN and leaflets LF that causes leaflets LF to coapt more completely. The clinician then may manipulate a delivery device to attach the wire (e.g., cut and tie the wire) to one or more respective anchors of the plurality of anchors 34 to fix wire 32 in place and maintain the cinching force.

Figure 4:
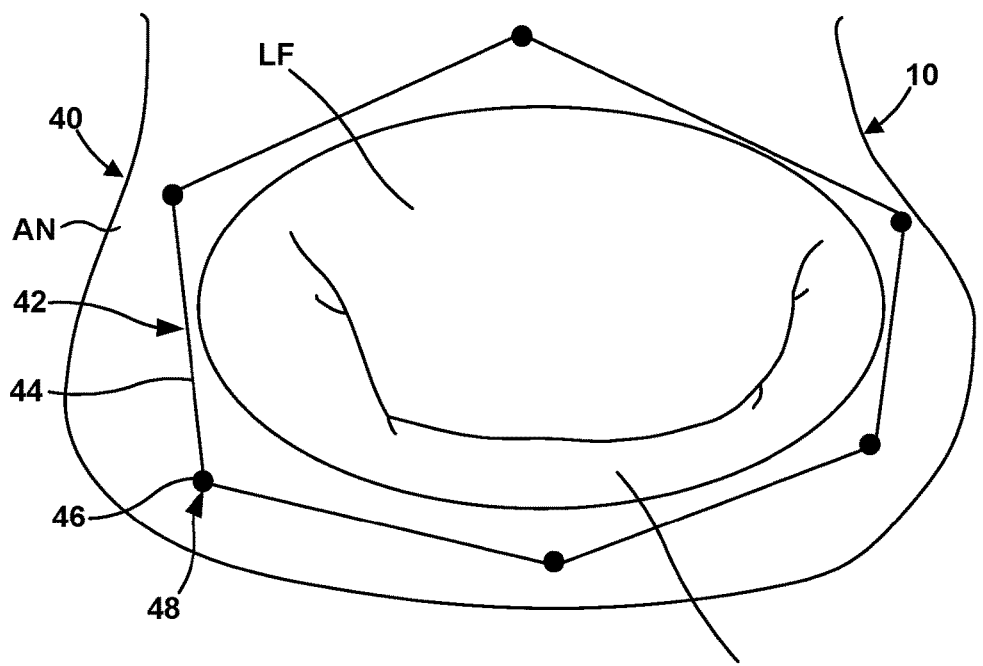
FIG. 4 is a schematic cross-sectional view of an example human heart and an example annuloplasty device including a wire including a plurality of straight sections joined by pivot points and a plurality of anchors.

In some examples, a wire may have a more complex shape than a general curve. For example, FIG. 4 is a schematic cross-sectional view of an example human heart 10 and an example annuloplasty device 40 including a wire 42 including a plurality of straight sections 44 joined by pivot points 46 and a plurality of anchors 48. Wire 42 may be similar to or substantially the same as any other wires described herein, including wire 22 of FIG. 2, aside from differences described herein. Similarly, plurality of anchors 34 may be similar to or substantially the same as any other anchors described herein, including plurality of anchors 24 of FIG. 2, aside from differences described herein.

Wire 42 includes a plurality of straight sections 44 joined by pivot points 46. Pivot points 46 define positions of wire that are configured to bend or pivot, and between which wire 42 maintains a substantially straight shape. Pivot points 46 may be integral with wire 42. For example, pivot points 46 may include coiled structures (e.g., helical or double helical coils, substantially planar coils, or the like). Wire 42 may include any suitable number of pivot points 46, e.g., at least two, at least three, at least four, at least five, or the like.

In some examples, pivot points 46 may define a predetermined angle between adjacent sections of wire 42. In some examples, the predetermined angle may be selected such that wire 42 defines a substantially continuous, enclosed annular shape.

Pivot points 46 also may define engagement sites the plurality of anchors 48. For examples, pivot points 46 may define a central bore or lumen through which a respective anchor of the plurality of anchors 48 extends. Further, the respective anchor of the plurality of anchors 48 may engage the respective pivot point 48, e.g., via an optional attachment feature, to engage wire 42.

Figure 5A:
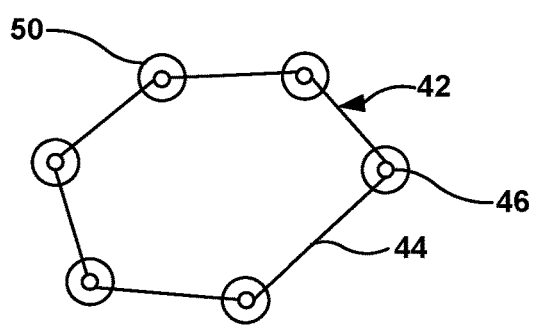
FIGS. 5A-5E are schematic views of the annuloplasty device of FIG. 4 in various configurations.

FIGS. 5A-5E are schematic views of the annuloplasty device 40 of FIG. 4 in various configurations. FIG. 5A is a schematic top view of annuloplasty device 40. In the example shown in FIG. 5A, annuloplasty device 40 includes wire 42 and length control elements 50. Wire 42 includes substantially straight sections 44 joined by pivot points 46. Pivot points 46 includes respective helical coils or other suitable anchors.

Length control elements 50 are mechanical structures having a physical shape configured to selectively engage with a respective inner diameter of each respective helical coil of pivot points 46. Length control elements 50 have an outer diameter that is greater than the respective inner diameters of pivot points 46. As such, when a respective length control element of length control elements 50 is engaged with a respective pivot point of pivot points 46, the respective length control element urges the coil of the pivot point to have a larger diameter, effectively increasing a distance between adjacent pivot points 46. On the other hand, when a respective length control element of length control elements 50 is disengaged with a respective pivot point of pivot points 46, the coil of the pivot point is allowed to recover toward a reduced diameter, decreasing a distance between adjacent pivot points 46. In which way, when annuloplasty device 40 is implanted and anchors 48 are engaged with annuloplasty device 40 and tissue while length control elements 50 are engaged with pivot points 46, and one or more length control elements 50 are subsequently removed, wire 42 may exert a radially inward force on the plurality of anchors 48 and the tissue to which the plurality of anchors 48 are engaged.

Figure 5B:
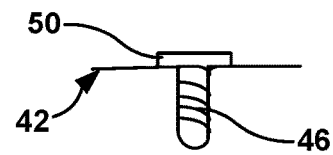

FIG. 5B is a schematic side view of annuloplasty device 40, showing wire 42, a pivot point 46, and a length control element 50. As shown in FIG. 5B, length control element 50 is disposed in a bore of a helical coil of pivot point 46 and urges the helical coil of pivot point 46 to a larger diameter.

Figure 5C:
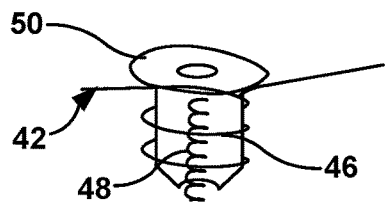

FIG. 5C is a schematic perspective view of annuloplasty device 40, showing wire 42, a pivot point 46, an anchor 48, and a length control element 50. As shown in FIG. 5C, length control element 50 is disposed in a bore of pivot point 46 and anchor 48 is disposed in a bore or lumen of length control element 50. In this way, anchor 48 may engage length control element 50 and anchor wire 42 with tissue.

Figure 5D:
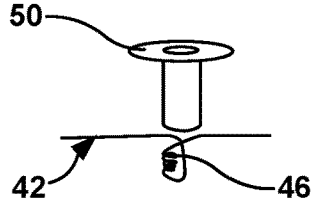

(FIG. 5D is a schematic perspective view of annuloplasty device 40, showing wire 42, a pivot point 46, and a length control element 50. Length control element 50 is removed from the bore of pivot point 46, allowing the helical coil of pivot point 46 to recover toward a smaller diameter than when length control element 50 is disposed in the bore.

Figure 5E:
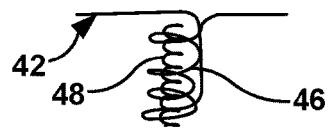

FIG. 5E is a schematic side view of annuloplasty device 40, showing wire 42, a pivot point 46, and anchor 48. Length control element 50 has been completely removed from the bore of pivot point 46 and the helical coil of pivot point 46 has recovered toward a smaller diameter. Anchor 48 is engaged with pivot point 46, thereby engaging wire 42 and anchoring wire 42 with tissue.

Annuloplasty device 40 may be delivered to and engaged with tissue of annulus AN using one or more delivery devices. In some examples, the plurality of anchors 48 and the plurality of length control elements 50 may be pre-engaged with or pre-assembled with wire 42 and delivered through a lumen of a single delivery device (e.g., a respective length control element may be engaged with each respective coil of pivot points 46 within the lumen, a respective anchor of the plurality of anchors 48 is engaged with each respective coil of pivot points 46 within the lumen, or both). Wire 42 may be configured to be in a substantially straight configuration within a lumen of the delivery device. A clinician may advance annuloplasty device 40 distally out of the lumen and position annuloplasty as desired using the delivery device. The clinician then may manipulate the delivery device to engage the plurality of anchors 48 with tissue of annulus AN and disengage the plurality of length control elements 50 from the plurality of pivot points 46 to cause wire 42 to exert a radially inward force on the plurality of anchors 48 and annulus AN.

In other examples, the plurality of anchors 48 are not engaged with wire 42 in the lumen of the delivery device, and may be delivered separately, using either the same delivery device or a second delivery device. In some examples, each respective pivot point of the plurality of pivot points 46 includes a guiding system or feature to facilitate engagement of an anchor of the plurality of with the pivot point once the pivot point is released from the lumen of the delivery device. In some examples, the guiding system or feature includes a ferromagnetic material configured to magnetically attract an anchor to the pivot point.

FIGS. 6A-6E are schematic views of an example annuloplasty device 60 including a wire ring 62 and a plurality of anchors 64, and a wire frame 66 including a plurality of hollow tubular struts 68. Wire ring 62 may be similar to or substantially the same as any other wires described herein, including wire 22 of FIG. 2, aside from differences described herein. Similarly, plurality of anchors 64 may be similar to or substantially the same as any other anchors described herein, including plurality of anchors 24 of FIG. 2, aside from differences described herein. Wire frame 66 facilitates delivery of the plurality of anchors 64 and wire ring 62 into engagement with annulus AN (FIGS. 1A and 1B).

Wire frame 66 includes a plurality of hollow tubular struts 68. Wire frame 66 may be housed in lumen of an anchor delivery device 70. A clinician may manipulate anchor delivery device 70 to advance distal ends of hollow tubular struts 68 from a distal port of anchor delivery device 70. A respective anchor of the plurality of anchors 64 is disposed in each respective hollow tubular strut of wire frame 66, as shown in FIG. 6B with respect to helix 72, which is an example of an anchor. In some examples, wire frame 66 may include a sheet or covering coupling the plurality of hollow tubular struts 68 to form a structure similar to an umbrella. In some examples, this may increase adaptability of wire frame 66 to variability in patient anatomy, e.g., different sized and shape annuluses AN.

In some examples, the plurality of hollow tubular struts 68 have a pre-set shape that the plurality of hollow tubular struts 68 recover toward upon exiting anchor delivery device 70. For example, the pre-set shape may result in the distal ends of the plurality of hollow tubular struts 68 together defining a circular or elliptical pattern in a plane defined by the distal ends of the plurality of hollow tubular struts 68 when extended from the distal port of anchor delivery device 70, as shown in FIG. 6A. In some examples, the plurality of hollow tubular struts 68 are formed from a biocompatible shape memory alloy, such as a Ni—Ti alloy. In other examples, a clinician may form the plurality of hollow tubular struts 68 into a desired shape, e.g., by expanding the struts away from each other using a balloon or the like. In some implementations, each hollow tubular strut may be individually actuatable, e.g., using a wire attached to the strut. In some of these examples, the plurality of hollow tubular struts 68 may be formed from any suitable material, such as, but not limited to stainless steel.

A clinician may manipulate anchor delivery device 70 to cause each respective anchor of the plurality of anchors 64 to advance out of the distal end of the respective hollow tubular struts 68 and engage the annulus AN (FIGS. 1A and 1B). In some examples, the plurality of anchors 64 each include a respective helix or double helix 72 and an optional attachment feature 74, as shown in FIG. 6C. Attachment feature 74 may be configured to engage and retain wire ring 62. For example, attachment feature 74 may include a hook, loop, or the like.

Wire ring 62 may be delivered to the treatment site using a wire delivery device. The wire delivery device may be configured to cause wire ring 62 to advance over the plurality of hollow tubular struts 68 and engage the plurality of anchors 64 after the anchors 64 are engaged to annulus AN (FIGS. 1A and 1B). For example, a clinician may manipulate the wire delivery device to coaxially advance over the anchor delivery device and release wire ring 62 coaxially around the plurality of hollow tubular struts 68. The clinician may manipulate the wire delivery device to advance wire ring 62 over the plurality of hollow tubular struts 68 and engage with each respective anchor of the plurality of anchors 64 (e.g., with respective attachment features 74).

In some examples, wire ring 62 includes at least one spring 76A and 76B configured to reduce a length of wire ring 62 and urge at least some anchors of the plurality of anchors 64 toward each other in the radially inward direction once the wire delivery device has released wire ring 62. In some examples, at least one spring 76A and 76B may be oriented longitudinally along the anteroposterior axis on the medial and lateral sides of wire ring 62. As wire ring 62 passes over the plurality of hollow tubular struts 68, the plurality of hollow tubular struts 68 may cause wire ring 62 to expand in circumference by deforming the least one spring 76A and 76B. The clinician may manipulate the wire delivery device to advance wire ring 62 over attachment features 74, then pull wire ring 62 into engagement with attachment features 74 and/or retract wire frame 66 to allow wire ring 62 to move radially inward under influence of at least one spring 76A and 76B to engage attachment features 74. At least one spring 76A and 76B of wire ring 62 may cause a septal-lateral diameter reduction of the annulus AN (FIGS. 1A and 1B).

Figure 7:
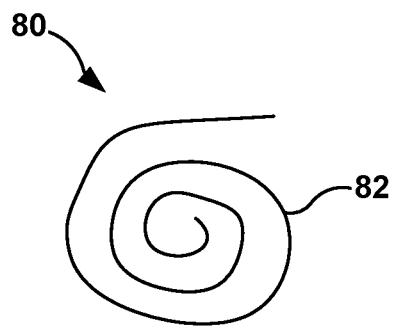
FIG. 7 is a schematic cross-sectional view of an example annuloplasty device including a wire having a pre-set shape.

FIG. 7 is a schematic cross-sectional view of an example annuloplasty device 80 including a wire 82 having a pre-set shape. Wire ring 82 may be similar to or substantially the same as any other wires described herein, including wire 22 of FIG. 2, aside from differences described herein. Wire 82 has a pre-set shape that is configured to be unrolled along annulus AN (FIGS. 1A and 1B). In some examples, wire 82 may have a non-circular cross-sectional shape, such as a crescent shape, an elliptical shape, a substantially flat shape, or the like. Annuloplasty device 80 additionally may include any of the anchors described herein and may be delivered and engaged to annulus AN (FIGS. 1A and 1B) in a similar manner to other annuloplasty devices described herein.

Figure 8:
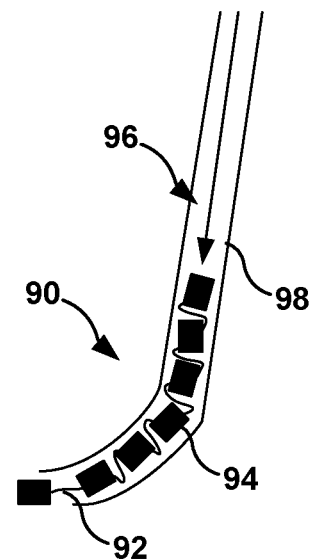
FIG. 8 is a schematic partial cross-sectional view of an example annuloplasty device including a wire and attached anchors disposed in a lumen of a delivery device.

FIG. 8 is a schematic partial cross-sectional view of an example annuloplasty device 90 including a wire 92 and attached a plurality of anchors 94 disposed in a lumen 96 of a delivery device 98. Wire 92 may be similar to or substantially the same as any other wires described herein, including wire 22 of FIG. 2, aside from differences described herein. Similarly, plurality of anchors 94 may be similar to or substantially the same as any other anchors described herein, including plurality of anchors 24 of FIG. 2, aside from differences described herein. Delivery device 98 may be used to delivery any of the annuloplasty devices described herein, including annuloplasty device 90.

Wire 92 may be pre-assembled with or pre-engaged to the plurality of anchors 94 while wire 92 is housed in lumen 96. Wire 92 may be looped or coiled within lumen 96 between respective anchors of the plurality of anchors 94. The plurality of anchors 94 may substantially stack within lumen 96 of delivery device 98.

A clinician may deliver and engage annuloplasty device 90 with annulus AN by manipulating delivery device 98 to advance an anchor of the plurality of anchors 94 out of lumen 96. For example, the clinician may manipulate delivery device 98 to apply a force to a proximal anchor within lumen 96, and annuloplasty device 90 may transmit the force to the distal-most anchor within lumen 96. Once an anchor of the plurality of anchors 94 has been released or advanced out of lumen 96, the clinician may manipulate delivery device 98 to cause the anchor to engage with tissue of annulus AN, e.g., by torquing the anchor. The clinician then may manipulate delivery device 98 to move a distal end of delivery device 98 adjacent to another selected location for placing an anchor and repeat the process of applying a force to a proximal anchor within lumen 96, causing the anchor to engage with tissue of annulus AN, and moving delivery device 98 to another location. Such a delivery technique may allow incremental cinching or tightening of wire 92 between specific anchors of the plurality of anchors 94, rather than only overall cinching or tightening of wire 92. This may allow greater control of where forces are applied to annulus AN.

Figure 9A:
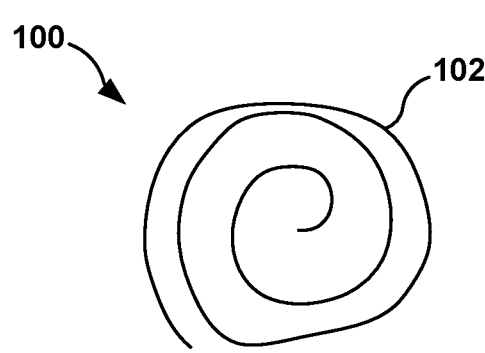
FIGS. 9A and 9B are schematic top and side views of an example annuloplasty device including a wire.
Figure 9B:
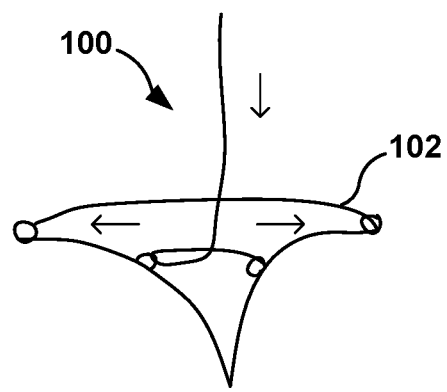

FIGS. 9A and 9B are schematic top and side views of an example annuloplasty device 100 including a wire 102. Wire 102 may be similar to or substantially the same as any other wires described herein, including wire 22 of FIG. 2, aside from differences described herein. Annuloplasty device 100 additionally may include any of the anchors described herein and may be delivered and engaged to annulus AN (FIGS. 1A and 1B) in a similar manner to other annuloplasty devices described herein. Wire 102 includes a conical coil having a gradually decreasing radius, which provides a mechanism to transform downward force into outward radial force. This may facilitate engagement of wire 102 with annulus AN.

Figure 10:
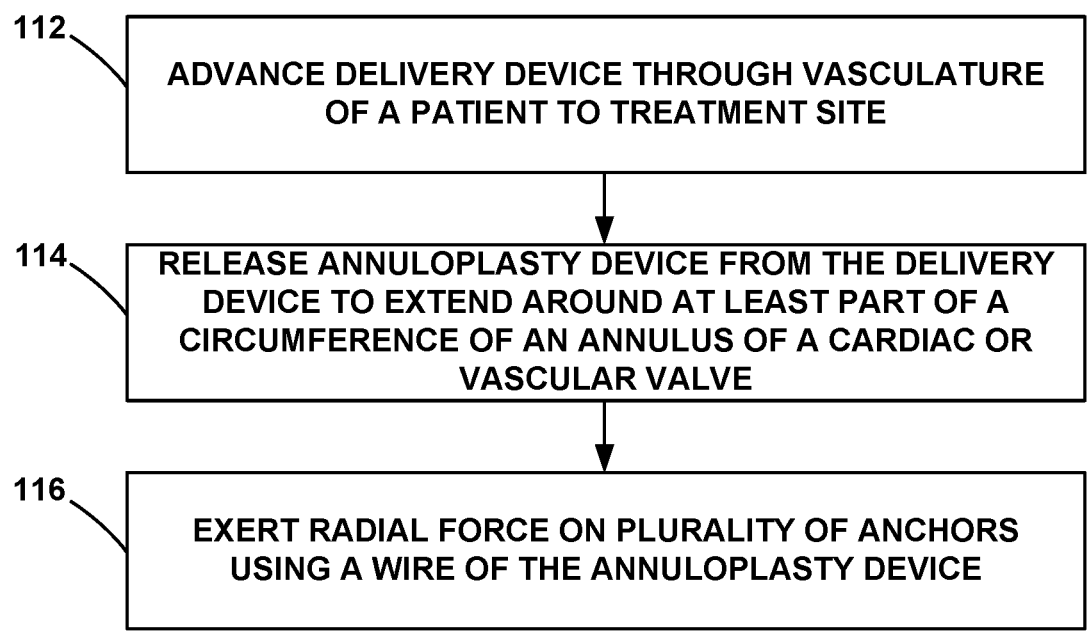
FIG. 10 is a flow diagram illustrating an example technique for implanting an annuloplasty device.

FIG. 10 is a flow diagram illustrating an example technique for implanting an annuloplasty device. The technique of FIG. 10 will be described with concurrent reference to annuloplasty device 20 of FIG. 2, although it will be understood that the technique of FIG. 10 may be used to implant any of the annuloplasty devices described herein, and the annuloplasty devices described herein may be implanted using other techniques.

Delivery device 26 may be advanced through vasculature of a patient to a treatment site (112). For example, a clinician may introduce delivery device 26 into vasculature of a patient transcutaneously. For instance, delivery device 26 may be introduced to a femoral or radial artery. Delivery device 26 may be advanced through vasculature of the patient to the treatment site by a clinician manipulating a handle of delivery device 26. In some examples, delivery device 26 may include a steerable shaft or tip to allow the clinician to direct delivery device 26 through bends, curves, and branching points of the vasculature.

In some examples, the treatment site may include the mitral valve, and delivery device 26 may be advanced to the left atrium. In other examples, the treatment site may include another heart valve. Delivery device 26 may access the left atrium trans-septally, trans-aortically, or trans-apically. In some examples, delivery device 26 may be tracked over a guide wire, through a guide catheter, or the like as delivery device 26 is advanced to the treatment site. Delivery device 26 may include one or more radiological markers at or near a distal end of delivery device 26 to assist visualizing delivery device 26 as delivery device is advanced to the treatment site.

Once delivery device 26 (e.g., a distal portion of delivery device 26) has been advance to the treatment site, delivery device 26 may release annuloplasty device 20, including wire 22 and the plurality of anchors 24 (114). For example, a clinician may manipulate delivery device 26 to release annuloplasty device 20 from a lumen of delivery device 26 to extend around at least part of a circumference of annulus AN of a cardiac or vascular valve. The clinician may manipulate delivery device 26 in any of the manners described herein. Delivery device 26 may include a single delivery device having a lumen housing wire 22 and the plurality of anchors 24, a single delivery device having a first lumen housing wire 22 and a second lumen housing the plurality of anchors 24, or a first wire delivery device and a second anchor delivery device.

Once annuloplasty device 20, including wire 22 and the plurality of anchors 24 have been released and engaged with tissue of annulus AN, wire 22 may be cinched or allowed to contract to exert a radial force on the plurality of anchors 24 and annulus AN (116).

As noted above, anchors used with the annuloplasty devices described herein, including annuloplasty device 20, are configured to engage with tissue in order to help secure the respective annuloplasty device in place in a heart of a patient. The plurality of anchors may include helices, double helices, hooks, or the like, and may include or omit an optional attachment feature for engaging wire 22. In addition, each anchor of the plurality of anchors may be engaged with tissue by, for example, "screwing" the anchor into tissue using a torquing force, by pushing the anchor into tissue using a pushing force, by suturing the anchor to tissue, or any combination thereof.

FIGS. 11A-11E illustrate side views of example anchors that may be used with the annuloplasty devices described herein. Each of the anchors shown in FIGS. 11A-11E are configured to be pushed into tissue, e.g., with or without any torquing force, in order to engage the anchor with tissue and fix the anchor in place within the tissue. While FIGS. 11A-11E are described with reference to annuloplasty device 20, in other examples, the anchors described with reference to FIGS. 11A-11E may be used with any annuloplasty device, including the other annuloplasty devices described herein.

Figure 11A:
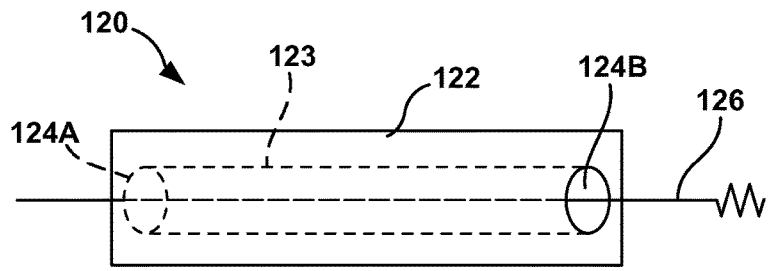
FIGS. 11A-11E illustrate side views of example anchors that may be used with the annuloplasty devices described herein

FIG. 11A illustrates a top view of an example anchor 120 and illustrates an example of how anchor 120 may be attached to wire 22 of annuloplasty device 20. Anchor 120 includes an anchor head 122 defining a through-bore 123. Ends 124A, 124B of through-bore 123 are open such that wire 22 may extend completely through through-bore 123 and out the ends 124A, 124B. In some examples, wire 22 is fixed to anchor head 122, while in other examples, wire 22 is configured to freely slide within bore 123 relative to anchor head 122. Anchor head 120 may be attached to or formed with any suitable anchor body that is configured to be inserted in tissue to fix anchor 120 to tissue. Anchor head 122 may include a larger cross-sectional diameter than the anchor body of anchor 120 (not shown in FIG. 11A).

Figure 11B:
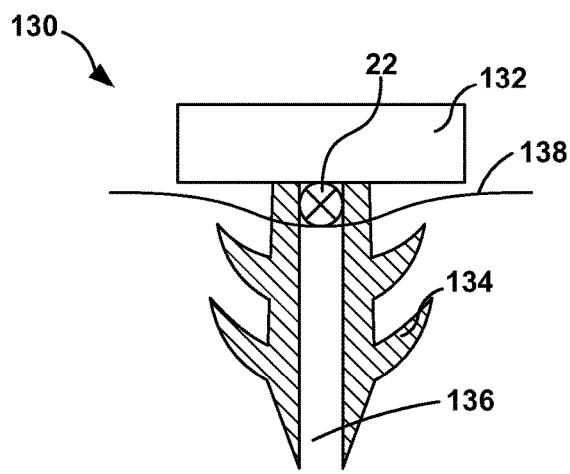

FIG. 11B illustrates a side view of another example anchor 130, which includes an anchor head 132 and an anchor body 134. Anchor 130 is configured to be connected to wire 22 (fixedly attached or in a relatively moveable configuration) using any suitable technique. In the example shown in FIG. 11B, anchor body 134 defines a lumen or other opening 136 through which wire 22 may extend. In some examples, wire 22 is fixed to anchor head 134 within opening 136, while in other examples, wire 22 is configured to freely slide relative to anchor head 132. In other examples, anchor head 132 may be similar to anchor head 122 (FIG. 11A). Anchor body 134 defines tissue engagement features (e.g., tines, barbs, or other protrusions) that are configured such that when anchor body 134 is pushed into tissue surface 138, anchor body 134 may readily move into the tissue, but may resist movement in an opposite direction, away from tissue surface 138. Anchor head 132 includes a larger cross-sectional diameter than anchor body 134, which helps prevent anchor 130 from inadvertently being completed embedded below tissue surface 138.

Figure 11C:
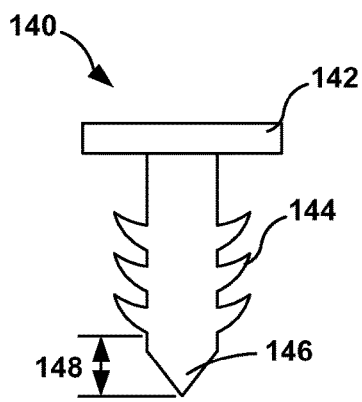
Figure 11D:
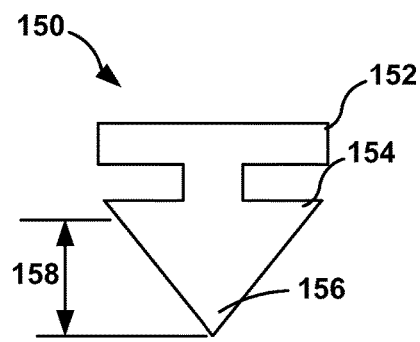
Figure 11E:
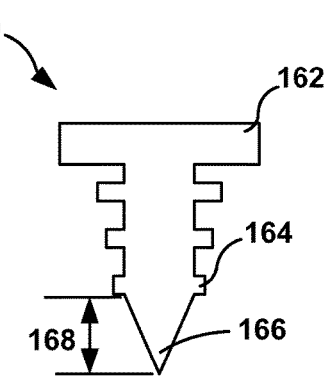

Other example anchor body configurations are shown in FIGS. 11C-11E. In FIG. 11C, example anchor 140 includes anchor head 142 and anchor body 144. FIG. 11D illustrates an example anchor 150, which includes anchor head 152 and anchor body 154. FIG. 11E illustrates an example anchor 160, which includes anchor head 162 and anchor boy 164.

Anchor heads 142, 152, 162 may each have any suitable configuration and may be, for example, configured like anchor head 122 (FIG. 11A) or anchor head 132 (FIG. 11B). Anchors 140, 150, 160 are configured to be connected to wire 22 using any suitable technique, such as, but not limited to, the techniques described with reference to FIGS. 11A and 11B. Anchor body 144 (FIG. 11C) and anchor body 164 (FIG. 11E) each define a plurality of protrusions similar to those defined by anchor body 134 of FIG. 11B, as well as a relatively sharp (e.g., incisive) tip 146, 166 that is configured to penetrate through tissue as anchor 140 is inserted into tissue. Anchor body 154 (FIG. 11D) defines a triangular-shaped cross-section defining a relatively sharp (e.g., incisive) tip 156 that is configured to penetrate through tissue as anchor 140 is inserted into tissue. The tapered profiles of anchor bodies 154, 164 (FIGS. 11D, 11E) may help facilitate entry of the respective anchor 150, 160 into tissue.

Anchor bodies 134, 144, 154, 164 may have any suitable length. In some examples, the distal portions of anchor bodies 134, 144, 154, 164 do not include any tissue engagement features (e.g., tines, barbs, or other protrusions) configured to engage with tissue so that the respective anchors 130, 140, 150, 160 can be partially deployed and subsequently repositioned. For example, the distal portion 148, 158, 168 of anchors 140, 150, 160, respectively, do not include any tissue engagement. In some examples, distal portion 148, 158, 168 of anchors 140, 150, 160 are about 20% to about 50%, such as about 30% to about 35%, or about 33%, of the total length of the respective anchor bodies 144, 154, 164. A length of an anchor body may be measured, for example, from the distal end of the respective anchor head to a distal-most part of the anchor body.

The following clauses illustrate example subject matter described herein.

Clause 1. An annuloplasty device comprising: a wire configured to extend around at least part of an annulus of a cardiac or vascular valve; and a plurality of anchors configured to: engage the wire, and anchor the wire to the annulus; wherein the wire is configured to urge at least some anchors of the plurality of anchors toward each other in a radially inward direction to decrease a distance between valve leaflets that extend from the annulus.

Clause 2. The annuloplasty device of clause 1, wherein the wire comprises a biocompatible shape memory alloy.

Clause 3. The annuloplasty device of clause 2, wherein the wire comprises a nickel-titanium alloy.

Clause 4. The annuloplasty device of any one of clauses 1 to 3, wherein the wire comprises at least one spring configured to reduce a length of the wire and urge at least some anchors of the plurality of anchors toward each other in the radially inward direction.

Clause 5. The annuloplasty device of any one of clauses 1 to 4, wherein the wire comprises a pre-set shape that is configured to urge at least some anchors of the plurality of anchors toward each other in the radially inward direction.

Clause 6. The annuloplasty device of any one of clauses 1 to 5, wherein the wire comprises a plurality of substantially straight segments connected by pivot points.

Clause 7. The annuloplasty device of clause 6, wherein the pivot points comprise coils formed by the wire.

Clause 8. The annuloplasty device of clause 6 or 7, further comprising a plurality of length control elements, wherein a respective length control element is configured to selectively engage with a respective inner diameter of each respective coil, wherein the coils are configured to assume a reduced diameter and urge adjacent anchors of the plurality of anchors toward each other when the respective length control element is disengaged from the respective coil.

Clause 9. The annuloplasty device of any one of clauses 6 to 8, wherein a respective anchor of the plurality of anchors is configured to engage with a respective pivot point.

Clause 10. The annuloplasty device of any one of clauses 1 to 9, wherein the wire comprises a pre-set shape configured to engage against the annulus.

Clause 11. The annuloplasty device of any one of clauses 1 to 10, wherein the plurality of anchors comprises a plurality of helical coils, wherein each helical coil defines a longitudinal axis.

Clause 12. The annuloplasty device of clause 11, wherein the plurality of helical coils comprises a plurality of conical helical coils.

Clause 13. The annuloplasty device of clause 11, wherein the plurality of helical coils comprises a plurality of double helical coils.

Clause 14. The annuloplasty device of any one of clauses 11 to 13, wherein at least one helical coil of the plurality of helical coils engages the wire with the wire passing through a bore of the helical coil substantially parallel to the longitudinal axis of the helical coil.

Clause 15. The annuloplasty device of any one of clauses 11 to 14, wherein at least one helical coil of the plurality of helical coils engages the wire with the wire passing through a coil circumference of the helical coil substantially perpendicular to the longitudinal axis of the helical coil.

Clause 16. The annuloplasty device of any one of clauses 1 to 15, wherein anchors of the plurality of anchors comprise respective attachment features configured to engage with the wire.

Clause 17. The annuloplasty device of clause 16, wherein the respective attachment features comprise hooks.

Clause 18. The annuloplasty device of any one of clauses 1 to 17, wherein the anchors comprise a biocompatible metal alloy.

Clause 19. The annuloplasty device of clause 18, wherein the wire comprises a nickel-titanium alloy.

Clause 20. The annuloplasty device of any one of clauses 1 to 19, wherein the cardiac or vascular valve comprises a mitral valve comprising a mitral annulus, an anterior valve leaflet, and a posterior valve leaflet, and wherein the wire is configured to extend around a circumference of the mitral annulus from proximate the anterior valve leaflet to proximate the posterior valve leaflet.

Clause 21. A system comprising: a delivery device configured to access vasculature of a patient; and the annuloplasty device of any one of clauses 1 to 20, wherein the delivery device is configured to deliver the annuloplasty device to the annulus of the cardiac or vascular valve and engage the anchors to the annulus.

Clause 22. The system of clause 21, wherein the plurality of anchors are configured to be preassembled with the wire when the wire is in a lumen of the delivery device, and wherein the plurality of anchors comprise a plurality of helical coils, wherein each helical coil defines a longitudinal axis, and wherein the wire passes through a respective bore of each respective helical coil with the wire substantially parallel to the longitudinal axis of the respective helical coil.

Clause 23. The system of clause 22, wherein the plurality of helical coils comprise a plurality of conical helical coils, wherein each conical helical coil comprises a wide end and a narrow end, and wherein the wide end of each conical helical coil is positioned toward a distal end of the wire.

Clause 24. The system of any one of clauses 21 to 23, wherein the delivery device is configured to apply a torquing force to the wire to cause an anchor of the plurality of anchors to rotate and engage the annulus.

Clause 25. The system of clause 21, wherein the wire comprises multiple straight segments connected by pivot points, and wherein the wire is configured to be in a substantially straight configuration within a lumen of the delivery device.

Clause 26. The system of clause 25, wherein each pivot point comprises a respective coil engaged with a respective length control element within the lumen of the delivery device.

Clause 27. The system of clause 25 or 26, wherein each pivot point is engaged with a respective anchor of the plurality of anchors within the lumen of the delivery device.

Clause 28. The system of clause 25 or 26, wherein the anchors of the plurality of anchors are not engaged with the wire in the lumen of the delivery device, and wherein each respective pivot point of the plurality of pivot points comprises a guiding system configured to facilitate engagement of an anchor with the pivot point once the pivot point is released from the lumen of the delivery device.

Clause 29. The system of clause 28, wherein the guiding system comprises a ferromagnetic material.

Clause 30. The system of clause 21, wherein the plurality of anchors is pre-assembled with the wire, and wherein the wire and the plurality of anchors are disposed within a common lumen within the delivery device.

Clause 31. The system of clause 30, wherein sections of the wire between the plurality of anchors are wound within the lumen.

Clause 32. The system of clause 21, wherein the delivery device comprises a first lumen and a second lumen, wherein the first lumen is substantially parallel to the second lumen, wherein the wire is disposed in the first lumen, and wherein the plurality of anchors are disposed in the second lumen.

Clause 33. The system of clause 32, wherein the first lumen and the second lumen are coupled such that the wire passes through the second lumen before exiting the delivery device.

Clause 34. The system of clause 33, wherein the first lumen and the second lumen are coupled such that the wire passes through the second lumen substantially perpendicular to a longitudinal axis of the second lumen.

Clause 35. The system of any one of clauses 32 to 34, wherein the first lumen and the second lumen are coupled such that the wire passes through a respective anchor of the plurality of anchors disposed in the second lumen before exiting the delivery device.

Clause 36. The system of clause 21, wherein the delivery device comprises a wire delivery device and an anchor delivery device, wherein the wire delivery device comprises a first lumen housing the wire, wherein the anchor delivery device comprises a second lumen housing the plurality of anchors.

Clause 37. The system of clause 36, wherein the wire delivery device is configured to cause the wire to distally exit the first lumen through a distal exit port of the wire delivery device, and wherein the anchor delivery device is configured to advance along or over the wire after the wire is deployed to engage the plurality of anchors with the wire and the annulus.

Clause 38. The system of clause 37, wherein the plurality of anchors comprises a plurality of helical coils, wherein each helical coil defines a longitudinal axis, and wherein the anchor delivery device is configured to engage the plurality of anchors such that the wire passes through a respective bore of each respective helical coil with the wire substantially parallel to the longitudinal axis of the respective helical coil.

Clause 39. The system of clause 38, wherein the plurality of helical coils comprises a plurality of conical helical coils, wherein each conical helical coil comprises a wide end and a narrow end, and wherein the wide end of each conical helical coil is positioned toward a distal end of the wire.

Clause 40. The system of any one of clauses 36 to 39, wherein the anchor delivery device is configured to torque the wire to cause the anchors to rotate and engage the annulus.

Clause 41. The system of any one of clauses 36 to 40, wherein the wire is engaged with a fixation device proximate to a distal end of the wire while the wire is disposed in the lumen of the wire delivery device.

Clause 42. The system of clause 36, further comprising a wire frame comprising a plurality of hollow tubular struts, wherein the wire frame is housed in the anchor delivery device, wherein the anchor delivery device is configured to advance distal ends of the hollow tubular struts from a distal port of the anchor delivery device, and wherein at least one anchor of the plurality of anchors is disposed in a respective hollow tubular strut of the wire frame.

Clause 43. The system of clause 36, wherein the hollow tubular struts are pre-set so that the distal ends of the hollow tubular struts together define a circular or elliptical pattern in a plane defined by the distal ends of the hollow tubular struts when extended from the distal port of the anchor delivery device.

Clause 44. The system of clause 42 or 43, wherein the anchor delivery device is further configured to cause each respective anchor to advance out of the distal end of the respective hollow tubular struts and engage the annulus.

Clause 45. The system of any one of clauses 42 to 44, wherein the hollow tubular struts comprise a biocompatible shape memory alloy.

Clause 46. The system of any one of clauses 42 to 45, wherein the plurality of anchors each comprise a respective attachment feature configured to engage the wire.

Clause 47. The system of any one of clauses 42 to 46, wherein the wire comprises a wire ring, and wherein the wire delivery device is configured to cause the wire ring to advance over the hollow tubular struts and engage the plurality of anchors after the anchors are engaged to the annulus.

Clause 48. The system of clause 47, wherein the wire comprises at least one spring configured to reduce a length of the wire and urge at least some anchors of the plurality of anchors toward each other in the radially inward direction.

Clause 49. A method comprising: advancing a delivery device through vasculature of a patient to a vascular or cardiac treatment site, wherein the delivery device comprises a lumen housing an annuloplasty device, wherein the annuloplasty device comprises: a wire configured to extend around at least part of a circumference of an annulus of a cardiac or vascular valve; and a plurality of anchors configured to: engage the wire, and anchor the wire to the annulus; wherein the wire is configured to urge at least some anchors of the plurality of anchors toward each other in a radially inward direction to decrease a distance between valve leaflets that extend from the annulus; and releasing the annuloplasty device from the lumen to extend around at least part of a circumference of an annulus of a cardiac or vascular valve.

Clause 50. The method of clause 49, wherein the wire comprises a biocompatible shape memory alloy.

Clause 51. The method of clause 49, wherein the wire comprises a nickel-titanium alloy.

Clause 52. The method of any one of clauses 49 to 51, wherein the wire comprises at least one spring configured to reduce a length of the wire and urge at least some anchors of the plurality of anchors toward each other in the radially inward direction, and wherein the delivery device is configured to release the wire after causing the wire to be engaged with the plurality of anchors, and wherein the at least one spring urge at least some anchors of the plurality of anchors toward each other in the radially inward direction upon being released by the delivery device.

Clause 53. The method of any one of clauses 49 to 52, wherein the wire comprises a pre-set shape that is configured to urge at least some anchors of the plurality of anchors toward each other in the radially inward direction, wherein the delivery device is configured to urge the wire away from the pre-set shape while the wire is disposed in the lumen of the delivery device, and wherein releasing the annuloplasty device from the lumen allows the wire to recover toward its pre-set shape.

Clause 54. The method of any one of clauses 49 to 53, wherein the wire comprises a plurality of substantially straight segments connected by pivot points, and wherein the delivery device is configured to urge the wire toward a substantially straight configuration while the wire is disposed in the lumen of the delivery device.

Clause 55. The method of clause 54, wherein the pivot points comprise coils formed by the wire.

Clause 56. The method of clause 54 or 55, wherein the annuloplasty device further comprises a plurality of length control elements engaged with pivot points.

Clause 57. The method of clause 56, further comprising removing, using the delivery device, a length control element to cause the coil engaged with the length control elements to compress and cause the wire to assume a reduced diameter and urge adjacent anchors of the plurality of anchors toward each other.

Clause 58. The method of any one of clauses 54 to 57, wherein a respective anchor of the plurality of anchors are configured to engage with each respective pivot point.

Clause 59. The method of any one of clauses 49 to 58, wherein the wire comprises a pre-set shape configured to engage against the valve annulus, wherein the delivery device is configured to urge the wire away from the pre-set shape while the wire is disposed in the lumen of the delivery device, and wherein releasing the annuloplasty device from the lumen allows the wire to recover toward its pre-set shape.

Clause 60. The method of any one of clauses 49 to 59, wherein advancing the delivery device through vasculature of the patient to the vascular or cardiac treatment site comprises advancing the delivery device through vasculature of the patient to a right atrium of the patient, and wherein the wire is configured to extend around a circumference of a mitral annulus of a mitral valve from proximate an anterior valve leaflet of the mitral valve to proximate a posterior valve leaflet of the mitral valve.

Clause 61. The method of clause 49, wherein the plurality of anchors are preassembled with the wire when the wire is in the lumen of the delivery device, and wherein the plurality of anchors comprise a plurality of helical coils, wherein each helical coil defines a longitudinal axis, and wherein the wire passes through a respective bore of each respective helical coil with the wire substantially parallel to the longitudinal axis of the respective helical coil.

Clause 62. The method of clause 61, wherein the plurality of helical coils comprises a plurality of conical helical coils, wherein each conical helical coil comprises a wide end and a narrow end, and wherein the wide end of each conical helical coil is positioned toward a distal end of the wire.

Clause 63. The method of any one of clauses 60 to 62, wherein releasing the annuloplasty device from the lumen of the delivery device comprises applying a torquing force to the wire to cause an anchor of the plurality of anchors to rotate and engage the annulus.

Clause 64. The method of clause 49, wherein the wire comprises multiple straight segments connected by pivot points, and wherein the wire housed in the lumen of the delivery device in a substantially straight configuration.

Clause 65. The method of clause 64, wherein each pivot point comprises a respective coil engaged with a respective length control element within the lumen of the delivery device.

Clause 66. The method of clause 64 or 65, wherein each pivot point is engaged with a respective anchor of the plurality of anchors within the lumen of the delivery device.

Clause 67. The method of clause 61 or 62, wherein the plurality of anchors are not engaged with the wire in the lumen of the delivery device, and wherein each respective pivot point of the plurality of pivot points comprises a guiding system configured to facilitate engagement of an anchor with the pivot point once the pivot point is released from the lumen of the delivery device, and wherein releasing the annuloplasty device from the lumen comprises: releasing the wire from the lumen of the delivery device, wherein the wire assumes a shape extending around at least part of a circumference of an annulus of a cardiac or vascular valve; and delivering a respective anchor to each respective pivot point after releasing the wire.

Clause 68. The method of clause 67, wherein the guiding system comprises a ferromagnetic material.

Clause 69. The method of clause 49, wherein the plurality of anchors is pre-loaded on the wire, wherein the wire and the plurality of anchors are disposed within a common lumen within the delivery device, and wherein the annuloplasty device from the lumen comprises: releasing a first anchor from the lumen; engaging the first anchor with the annulus at a first location of the annulus; releasing a portion of the wire between the first anchor and a second anchor from the lumen; releasing a second anchor from the lumen; and engaging the second anchor with the annulus at a second location of the annulus different from the first location.

Clause 70. The method of clause 69, wherein sections of the wire between the plurality of anchors are wound within the lumen of the delivery device, and wherein releasing the portion of the wire between the first anchor and the second anchor allows the wire to unwind.

Clause 71. The method of clause 49, wherein the lumen comprises a first lumen, wherein the delivery device further comprises a second lumen, wherein the first lumen is substantially parallel to the second lumen, wherein the wire is disposed in the first lumen, and wherein the plurality of anchors is disposed in the second lumen.

Clause 72. The method of clause 71, wherein the first lumen and the second lumen are coupled such that the wire passes through the second lumen before exiting the delivery device, and wherein releasing the annuloplasty device from the lumen comprises passing the wire from the first lumen through the second lumen and out of the delivery device.

Clause 73. The method of clause 72, wherein the first lumen and the second lumen are coupled such that the wire passes through the second lumen substantially perpendicular to a longitudinal axis of the second lumen.

Clause 74. The method of any one of clauses 71 to 73, wherein the first lumen and the second lumen are coupled such that the wire passes through a respective anchor of the plurality of anchors disposed in the second lumen before exiting the delivery device, and wherein releasing the annuloplasty device from the lumen comprises passing the wire from the first lumen through the second lumen to engage a the respective anchor and out of the delivery device.

Clause 75. The method of clause 49, wherein the delivery device comprises a wire delivery device and an anchor delivery device, wherein the wire delivery device comprises a first lumen housing the wire, wherein the anchor delivery device comprises a second lumen housing the wire, and wherein releasing the annuloplasty device from the lumen comprises: releasing the wire from the first lumen of the wire delivery device; and releasing the plurality of anchors from the second lumen of the anchor delivery device.

Clause 76. The method of clause 75, wherein releasing the wire from the first lumen of the wire delivery device comprises causing the wire to distally exit the first lumen through a distal exit port of the wire delivery device, and wherein releasing the plurality of anchors from the second lumen of the anchor delivery device comprises advancing the anchor delivery device along or over the wire after the wire is deployed to engage the plurality of anchors with the wire and the annulus.

Clause 77. The method of clause 76, wherein the plurality of anchors comprise a plurality of helical coils, wherein each helical coil defines a longitudinal axis, and wherein advancing the anchor delivery device along or over the wire after the wire is deployed to engage the plurality of anchors with the wire and the annulus comprises engaging the plurality of anchors such that the wire passes through a respective bore of each respective helical coil with the wire substantially parallel to the longitudinal axis of the respective helical coil.

Clause 78. The method of clause 76, wherein the plurality of helical coils comprises a plurality of conical helical coils, wherein each conical helical coil comprises a wide end and a narrow end, and wherein the wide end of each conical helical coil is positioned toward a distal end of the wire.

Clause 79. The method of any one of clauses 75 to 78, wherein releasing the annuloplasty device from the lumen comprises torquing the wire using the anchor delivery device to cause the anchors to rotate and engage the annulus.

Clause 80. The method of any one of clauses 75 to 79, wherein the wire is engaged with a fixation device proximate to a distal end of the wire while the wire is disposed in the lumen of the wire delivery device.

Clause 81. The method of clause 75, wherein the anchor delivery device further comprises a wire frame comprising a plurality of hollow tubular struts, wherein the wire frame is housed in the anchor delivery device, further comprising advancing distal ends of the hollow tubular struts from a distal port of the anchor delivery device, and wherein a respective anchor of the plurality of anchors is disposed in each respective hollow tubular strut of the wire frame.

Clause 82. The method of clause 81, wherein the hollow tubular struts are pre-set so that the distal ends of the hollow tubular struts together define a circular or elliptical pattern in a plane defined by the distal ends of the hollow tubular struts when extended from the distal port of the anchor delivery device.

Clause 83. The method of clause 81 or 82, further comprising causing, using the anchor delivery device, each respective anchor to advance out of the distal end of the respective hollow tubular struts and engage the annulus.

Clause 84. The method of any one of clauses 81 to 83, wherein the hollow tubular struts comprise a biocompatible shape memory alloy.

Clause 85. The method of any one of clauses 81 to 84, wherein the plurality of anchors each comprise a respective attachment feature configured to engage the wire.

Clause 86. The method of any one of clauses 81 to 85, wherein the wire comprises a wire ring, and wherein releasing the wire from the first lumen of the wire delivery device comprises causing the wire ring to advance over the hollow tubular struts and engage the plurality of anchors after the anchors are engaged to the annulus.

Clause 87. The method of clause 86, wherein the wire comprises at least one spring configured to reduce a length of the wire and urge at least some anchors of the plurality of anchors toward each other in the radially inward direction.

Clause 88. The method of any one of clauses 49 to 87, wherein releasing the annuloplasty device from the lumen comprises cinching the wire to urge at least some anchors of the plurality of anchors toward each other in a radially inward direction to decrease the distance between valve leaflets that extend from the annulus.

Various examples have been described. These and other examples are within the scope of the following claims.

What is claimed is:

1. An annuloplasty device comprising:
   a wire having a plurality of substantially straight segments connected by pivot points comprising coils formed by the wire, the wire configured to extend around at least part of an annulus of a cardiac or vascular valve;
   a plurality of anchors configured to:
      engage the wire, and
      anchor the wire to the annulus; and
   a plurality of length control elements, wherein a respective length control element is configured to selectively engage with a respective inner diameter of each respective coil, wherein the coils are configured to assume a reduced diameter and urge adjacent anchors of the plurality of anchors toward each other when the respective length control element is disengaged from the respective coil,
   wherein the wire is configured to urge at least some anchors of the plurality of anchors toward each other in a radially inward direction to decrease a distance between valve leaflets that extend from the annulus.

2. The annuloplasty device of claim 1, wherein the wire comprises a biocompatible shape memory alloy or a nickel-titanium alloy.

3. The annuloplasty device of claim 1, wherein the wire comprises a pre-set shape that is configured to urge at least some anchors of the plurality of anchors toward each other in the radially inward direction.

4. The annuloplasty device of claim 1, wherein a respective anchor of the plurality of anchors is configured to engage with a respective pivot point.

5. The annuloplasty device of claim 1, wherein the wire comprises a pre-set shape configured to engage against the annulus.

6. The annuloplasty device of claim 1, wherein the plurality of anchors comprises a plurality of helical coils, wherein each helical coil defines a longitudinal axis.

7. The annuloplasty device of claim 1, wherein anchors of the plurality of anchors comprise respective attachment features configured to engage with the wire.

8. The annuloplasty device of claim 1, wherein the anchors comprise a biocompatible metal alloy or a nickel-titanium alloy.

9. The annuloplasty device of claim 1, wherein the cardiac or vascular valve comprises a mitral valve comprising a mitral annulus, an anterior valve leaflet, and a posterior valve leaflet, and wherein the wire is configured to extend around a circumference of the mitral annulus from proximate the anterior valve leaflet to proximate the posterior valve leaflet.

* * * * *